(12) United States Patent
Podmore et al.

(10) Patent No.: US 12,702,473 B2
(45) Date of Patent: Aug. 11, 2026

(54) SYSTEMS FOR IMPROVING THE APPEARANCE OF TISSUE

(71) Applicant: REVELLE AESTHETICS, INC., Mountain View, CA (US)

(72) Inventors: Jonathan Podmore, San Carlos, CA (US); Earl Bright, II, Sunnyvale, CA (US); Joshua Makower, Los Altos Hills, CA (US); Arthur Ferdinand, Gilroy, CA (US); Amanda White, Mountain View, CA (US); Pablo Acosta, Newark, CA (US); John Hanley, Manhattan Beach, CA (US)

(73) Assignee: Revelle Aesthetics, Inc., Mountain View, CA (US)

( * ) Notice: Subject to any disclaimer, the term of this patent is extended or adjusted under 35 U.S.C. 154(b) by 967 days.

(21) Appl. No.: 17/866,694

(22) Filed: Jul. 18, 2022

(65) Prior Publication Data

US 2022/0354565 A1 Nov. 10, 2022

Related U.S. Application Data

(63) Continuation of application No. PCT/US2021/013885, filed on Jan. 19, 2021.

(Continued)

(51) Int. Cl.

| | |
|---|---|
| ***A61B 18/14*** | (2006.01) |
| ***A61B 17/32*** | (2006.01) |

(Continued)

(52) U.S. Cl.

CPC .......... *A61B 18/1482* (2013.01); *A61B 34/10* (2016.02); *A61B 2017/320056* (2013.01);

(Continued)

(58) Field of Classification Search

CPC ................ A61B 18/1482; A61B 34/10; A61B 2018/00904

See application file for complete search history.

(56) References Cited

U.S. PATENT DOCUMENTS

| | | |
|---|---|---|
| 3,704,711 A | 12/1972 | Park |
| 4,444,185 A | 4/1984 | Shugar |

(Continued)

FOREIGN PATENT DOCUMENTS

| | | |
|---|---|---|
| CN | 2504047 Y | 8/2002 |
| CN | 201617909 | 11/2010 |

(Continued)

OTHER PUBLICATIONS

Extended European Search Report for European Application No. 19841959.0, dated Mar. 23, 2022, 8 Pages.

(Continued)

*Primary Examiner* — Annie L Shoulders
(74) *Attorney, Agent, or Firm* — Blank Rome LLP

(57) ABSTRACT

Systems and methods for treating tissue including an apparatus that applies or a method involving separating septa to eliminate or reduce the appearance of cellulite or liposuction in combination with separating septa to eliminate or reduce the appearance of cellulite. In one approach, an interventional tool is placed between tissue layers to engage and treat tissue layers between which fat deposits are contained.

27 Claims, 12 Drawing Sheets

Related U.S. Application Data

(60) Provisional application No. 62/963,596, filed on Jan. 21, 2020.

(51) Int. Cl.

| | |
|---|---|
| ***A61B 18/00*** | (2006.01) |
| ***A61B 34/10*** | (2016.01) |
| *A61B 90/00* | (2016.01) |
| *A61B 90/30* | (2016.01) |

(52) U.S. Cl.

CPC ............... *A61B 2018/00601* (2013.01); *A61B 2018/00678* (2013.01); *A61B 2018/00702* (2013.01); *A61B 2018/00904* (2013.01); *A61B 2034/105* (2016.02); *A61B 2034/107* (2016.02); *A61B 2090/064* (2016.02); *A61B 2090/306* (2016.02)

(56) References Cited

U.S. PATENT DOCUMENTS 5,113,476 A 5/1992 Okada et al.
5,478,347 A 12/1995 Aranyi
5,649,947 A 7/1997 Auerbach et al.
5,728,112 A 3/1998 Yoon
5,749,147 A 5/1998 Hasegawa
6,165,188 A 12/2000 Saadat et al.
6,377,854 B1 4/2002 Knowlton
6,447,527 B1 9/2002 Thompson et al.
7,179,272 B2 2/2007 Kieturakis et al.
7,217,265 B2 5/2007 Hennings et al.
7,442,192 B2 10/2008 Knowlton
7,671,423 B2 3/2010 Voldman
7,771,374 B2 8/2010 Slatkine
7,871,423 B2 1/2011 Livneh
8,167,280 B2 5/2012 Chomas et al.
8,348,867 B2 1/2013 Deem et al.
8,439,940 B2 5/2013 Chomas et al.
8,652,123 B2 2/2014 Gurtner
8,979,881 B2 3/2015 Clark, III
9,358,033 B2 6/2016 Ballakur et al.
9,539,439 B2 1/2017 Jones et al.
9,550,052 B2 1/2017 Ignon et al.
9,615,882 B2 4/2017 Shroff et al.
9,919,168 B2 3/2018 Altshuler et al.
9,974,519 B1 5/2018 Schwarz et al.
10,117,892 B2 11/2018 Perry
10,251,669 B2 4/2019 Pomahac et al.
10,271,866 B2 4/2019 Clark, III
10,549,110 B1 2/2020 Schwarz
10,603,101 B2 3/2020 Weber
10,888,348 B2 1/2021 Gutwein et al.
11,013,527 B1 5/2021 Podmore et al.
11,116,888 B2 9/2021 Bright, II et al.
11,974,767 B2 5/2024 Makower et al.
2001/0025190 A1 9/2001 Weber et al.
2003/0032950 A1 2/2003 Altshuler et al.
2003/0130628 A1 7/2003 Duffy
2003/0158566 A1 8/2003 Brett
2003/0187457 A1 10/2003 Weber
2004/0049251 A1 3/2004 Knowlton
2004/0204734 A1* 10/2004 Wagner .......... A61B 17/320016 606/190
2004/0206365 A1 10/2004 Knowlton
2004/0215101 A1 10/2004 Rioux et al.
2004/0243159 A1 12/2004 Shiuey
2004/0260210 A1 12/2004 Ella et al.
2005/0251120 A1 11/2005 Anderson et al.
2006/0036164 A1 2/2006 Wilson et al.
2006/0074313 A1 4/2006 Slayton et al.
2006/0161253 A1 7/2006 Lesh
2006/0172255 A1 8/2006 Hochman et al.
2006/0241663 A1 10/2006 Rice et al.
2006/0241673 A1 10/2006 Zadini et al.
2006/0293722 A1 12/2006 Slatkine et al.
2007/0005091 A1 1/2007 Zadini et al.
2008/0006551 A1 1/2008 Tolley et al.
2008/0015624 A1 1/2008 Sonoda et al.
2008/0051627 A1 2/2008 Raju
2008/0058603 A1 3/2008 Edelstein et al.
2008/0109023 A1 5/2008 Greer
2008/0200863 A1 8/2008 Chomas et al.
2008/0275569 A1 11/2008 Lesh
2009/0093737 A1 4/2009 Chomas et al.
2009/0248004 A1 10/2009 Altshuler et al.
2009/0275899 A1 11/2009 Deem et al.
2010/0057056 A1* 3/2010 Gurtner .......... A61B 17/320016 606/45
2010/0106063 A1 4/2010 Chomas et al.
2010/0137799 A1 6/2010 Imai
2010/0228182 A1* 9/2010 Clark, III ............... A61B 18/20 606/171
2010/0237163 A1 9/2010 Chomas et al.
2010/0256596 A1 10/2010 Chomas
2010/0331820 A1 12/2010 Prisco et al.
2011/0028898 A1 2/2011 Clark, III et al.
2011/0295297 A1 12/2011 Shirley et al.
2011/0319839 A1 12/2011 Del Vecchio
2012/0022510 A1 1/2012 Welches et al.
2012/0150208 A1 6/2012 Messmer
2013/0123771 A1 5/2013 Clark, III et al.
2013/0190739 A1 7/2013 Clark, III et al.
2013/0190740 A1 7/2013 Clark, III et al.
2013/0197427 A1 8/2013 Merchant et al.
2013/0197515 A1 8/2013 Raybin et al.
2014/0257272 A1 9/2014 Clark, III et al.
2014/0276693 A1* 9/2014 Altshuler ............... A61B 18/20 606/14
2014/0335072 A1 11/2014 Hart
2015/0025420 A1* 1/2015 Slayton ................ A61B 8/4483 601/2
2015/0064165 A1 3/2015 Perry et al.
2015/0216719 A1 8/2015 DeBenedictis et al.
2016/0051314 A1 2/2016 Batchelor et al.
2016/0151646 A1 6/2016 Bonutti et al.
2016/0346037 A1 12/2016 Truckai et al.
2017/0172619 A1 6/2017 Kirkemo
2018/0000504 A1 1/2018 Knowlton
2018/0116905 A1 5/2018 Capelli et al.
2018/0214169 A1 8/2018 Gutwein et al.
2018/0250217 A1 9/2018 Davidson et al.
2019/0046738 A1 2/2019 Banker
2020/0046391 A1 2/2020 Capelli et al.
2020/0187971 A1 6/2020 Clark, III et al.
2020/0305918 A1 10/2020 Fogg et al.
2021/0093898 A1 4/2021 Pooth et al.
2021/0137551 A1 5/2021 Makower et al.
2021/0138127 A1 5/2021 Makower et al.
2022/0183714 A1 6/2022 Podmore et al.
2022/0233259 A1 7/2022 Thompson et al.
2022/0347496 A1 11/2022 Podmore et al.
2023/0255678 A1 8/2023 Podmore et al.

FOREIGN PATENT DOCUMENTS

CN 202154724 3/2012
CN 102721841 A 10/2012
CN 202821527 3/2013
CN 103313663 A 9/2013
CN 204191319 3/2015
CN 104644244 5/2015
CN 204500879 7/2015
CN 208335023 U 1/2019
EP 2504047 10/2012
GB 2350080 A 11/2000
JP H11218652 A 8/1999
JP 3020409 B2 3/2000
JP 2013526967 A 6/2013
JP 2018010292 A 1/2018
WO 1991002493 A1 3/1991
WO 2016040820 A1 3/2016
WO 2017176800 A1 10/2017
WO 2017192394 A1 11/2017

(56) References Cited

FOREIGN PATENT DOCUMENTS

| | | |
|---|---|---|
| WO | WO2019060924 | 3/2019 |
| WO | 2019164836 A1 | 8/2019 |
| WO | 2020023412 A1 | 1/2020 |

OTHER PUBLICATIONS

Extended European Search Report for European Application No. 20861414.9, dated Sep. 1, 2023, 12 Pages.
International Search Report and Written Opinion for International Application No. PCT/US2019/042865, dated Nov. 14, 2019, 7 Pages.
International Search Report and Written Opinion for International Application No. PCT/US2019/042871, dated Oct. 31, 2019, 6 Pages.
International Search Report and Written Opinion for International Application No. PCT/US2020/049590, dated Dec. 10, 2020, 6 Pages.
International Search Report and Written Opinion for International Application No. PCT/US2024/025149, dated Oct. 8, 2024, 12 Pages.

* cited by examiner

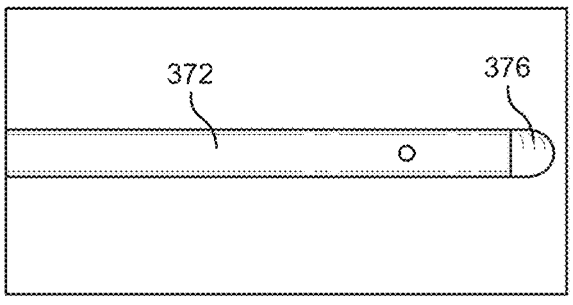
FIG. 8A
FIG. 8B
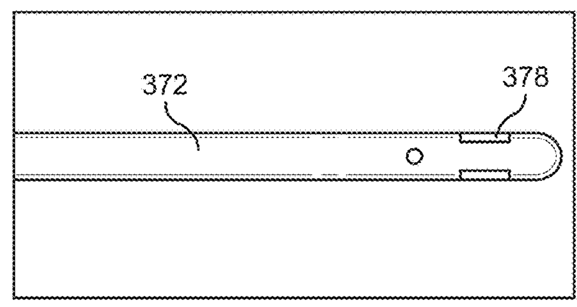
FIG. 8C
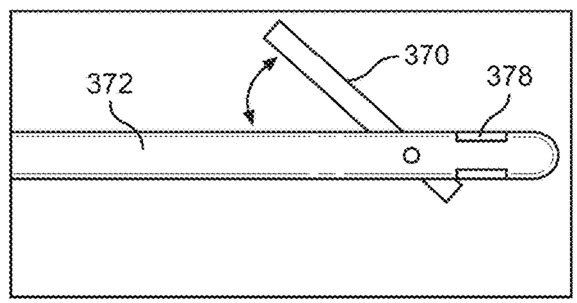
FIG. 8D
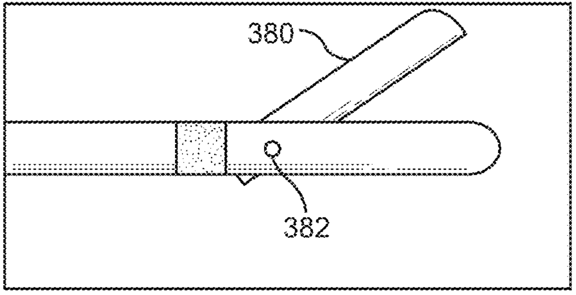
FIG. 8E

SYSTEMS FOR IMPROVING THE APPEARANCE OF TISSUE

FIELD OF THE DISCLOSURE

The present disclosure generally relates to systems and methods for approving the appearance of tissue.

BACKGROUND OF THE DISCLOSURE

There is a continuing need for an effective approach to liposuction, known as a method of improving the appearance of tissue by removing fat. Liposuction has become a widely accepted procedure for removing undesirable localized fat tissue, especially in areas that may be unresponsive to diet or exercise. This procedure is effective in removing excess accumulations of fat from various parts of the body.

However, conventional liposuction is often limited by septa, which are fibrous connections between the skin and muscle layers. Such septa also are a key to treating cellulite. In particular, cellulite is a septa focused condition that can be improved with cutting septa during a liposuction. Accordingly, combining the treatment of septa with liposuction can be used in a system to create a better appearance of tissue. Additionally, a cellulite treatment procedure can involve septa cutting without also conducting liposuction to thereby provide skin with an improved appearance.

It has been reported that more than 85% of women have cellulite thus suggesting that cellulite is a physiologic rather than pathologic condition. Cellulite is also known as gynoid lipodystrophy, nodular liposclerosis, edematofibrosclerotic panniculopathy, panniculosis, adiposis edematosa, demopanniculosis deformans or status protrusus cutis. There is a need for proactive treatment modalities that prevent future or reoccurrence of cellulite and which are easy and effective to use. The existence of fat in the reticular dermis alone is not thought to cause cellulite. Cellulite can be described as the herniation of subcutaneous fat within fibrous connective tissue that is expressed as dimpling of the skin. This fat loading can lead to stress on connective tissue located between fat lobulas. Such dimpling is more common in women than men due to the orientation of subcutaneous fibrous structures defining chambers containing fat cells. In fact, it is this structure that is believed to cause the appearance of cellulite more than being overweight. Often, cellulite appears on the pelvic region including the buttocks, lower limbs and abdomen.

Subdermal fat layers below the epidermis are contained between dermal layers connected by septa which act as connective tissue between the dermal layers. In men, the septa are arranged more randomly and densely oriented in a more criss-crossed configuration while the septa in women are generally more parallel in arrangement. Also, men have thicker dermis and more angled septa relative to the skin surface whereas women have relatively thinner dermis which thins with age, and septa that are perpendicular to the skin surface. Moreover, women with cellulite have exhibited thickening of the septa in the regions of cellulite and tensioning of septa highlights cellulite. In women, fat storage in adipose tissue has a biological purpose in that it is maximized ensuring adequate caloric availability for pregnancy and lactation. An increase in fluid retention or proliferation of adipose tissue in such subdermal fat layers can further result in the appearance of cellulite where the septa is maintaining a first distance between dermal layers, thus creating dimples, whereas pockets between septa bulge. Over time, the septa may stretch, then eventually contract and harden thus retaining tissue layers at fixed distances, but pockets between such septa may be expanded thus adding to the appearance of cellulite.

Various approaches have been taken to treat or address cellulite. Early treatments involved attempts at increasing circulation and fat oxidation in areas exhibiting cellulite. Here, substances such as hyaluronic acid and aminophylline were injected in the target areas to reduce cellulite. Other approaches involved electroporating the target areas followed by the application of mesotherapy, or applying dermological creams or other supplements to cellulite. These approaches could be supplemented by massage or massage was used alone for the purpose of promoting increased fat reabsorption or drainage of fluids and toxins in the treated areas. Ultrasound has also been proposed to disrupt subcutaneous tissues and fat and has been used in combination with liposuction. Low acoustic pressure in combination with the infiltration of microbubbles has also been employed to reduce the appearance of cellulite, as has the use of other energies such as lasers and radio frequency. Such approaches have been characterized by limited or unpredictable results. More recently, the cutting of septa with blades or needles in the subdermal region has been employed. Prior approaches have been found to be labor intensive and very traumatic to the tissue leading to bleeding, bruising, tissue nodules, subcutaneous scarring, calcified seromas, long, painful recoveries and inconsistent results.

Accordingly, there is a need for effective and efficient approaches to liposuction involving treating, minimizing or eliminating cellulite with simple systems that minimize trauma in combination with a liposuction procedure. These approaches should be associated with predictable results and be relatively easy to employ.

The present disclosure addresses these and other needs.

SUMMARY OF THE DISCLOSURE

Briefly and in general terms, the present disclosure is directed towards methods and devices for performing liposuction and cellulite treatment systems and methods. In various approaches, apparatus that facilitates and methods involving, depending on the system used and force applied by the user, stretching, re-orienting, disrupting, cutting, slicing, and/or tearing septum or septa in a location of cellulite. In one aspect, the treatment approach involves a tissue cutting or slicing system.

In one embodiment, a cellulite treatment device is mounted at a distal end portion of a liposuction cannula and is sized and shaped to be advanced between tissue layers. In one particular aspect, fibrous septa that connect superior and inferior fascia plateaus within skin can be crossed with the treatment device using one or more of an array of tools to engage, and depending on the tool used and force applied by the user, stretch, re-orient, tear, disrupt, cut or slice septa. By doing so, the target subcutaneous connective tissue associated with the surface defect can be directly modified with minimal impact to surrounding blood vessels and lymphatic system and fat can be more evenly distributed and skin can assume a smoother appearance.

Identification and assessment of target septa is accomplished by pushing, pulling or otherwise tensioning septa in areas believed to be associated with the expression of cellulite on the outside of skin. It has been recognized that septa causing a dimple or depression are located at various angles and locations relative to the dimple or depression observed on the skin and are not necessarily directly below such expressions of cellulite, and the treatment system and method is configured to identify the septa responsible for the appearance of cellulite that has been marked on the skin and target treatment on those septa and leave adjacent septa, blood vessels, etc. intact. Moreover, a range such as a small subset or a larger number of septa can be the structure causing a particular depression or dimple.

In one aspect, a tissue cutting device is provided which is coupled to a liposuction cannula. The cutting element is movable from a stored position to a cutting position so that the user may elect when to cut tissue. The cutting element permits the user to cut tissue adjacent to the cannula without removing the cannula from the incision site. In this manner, the user can position the liposuction wand adjacent to an area where the user desires to remove additional fat deposits that cannot be accessed due to tissue such as septa. The cutting element is then used to selectively cut tissue and the septa adjacent to the cannula. The cutting element is then retracted such that tissue not intended to be cut is unaffected. The cannula may then be moved so that the distal tip is positioned in the area where the tissue has been cut and the user then accesses the area having additional fat deposits with the cannula. The cannula can be made to be flexible to facilitate navigation into new areas of tissue.

Remote imaging or ultrasonic or fluoroscopic energy can be employed to observe the procedure. Further, anti-inflammatory, collagenase, deoxycholic acid, salicylic acid, glycolic acid, hyaluronic acid or cellulite treatment medicants can be employed at the interventional site separately or directly by the interventional device or other procedural instrumentation. In another aspect, the cutting device has the ability to provide the user with direct visualization of the cutting area. Light energy is employed to facilitate such direct visualization. For example, the cutting device can be mated with a fiberscope or have a video-capable microchip (e.g. CMOS or CCD) contained in the distal tip. Direct visualization enables the user to see what is captured by the cutting device before electing whether or not to cut the tissue. Aspects of the current disclosure include specific identification of the septa responsible for the cellulite appearance, severing or separation of those septa, confirmation intra-operatively of the separation of those septa was accomplished and the prevention of the re-appearance of the cellulite.

In various aspects, the treatment device can include one or more of projecting linkages, side opening hooks or V-shaped structure, a blade, or harmonic scalpel, selective cautery structure or energy transmitting structure for disrupting, cutting, slicing or dissecting tissue and/or controlling bleeding. In one particular approach, the treatment device includes a mechanical septa cutting element, such as a blade or sharpened surface, that cooperates with a septa hooking element to both hook then cut, slice, tear or disrupt septa. One or more of the septa hooking element and the septa cutting element is convertible from a hooking configuration to a cutting configuration and from a cutting configuration to a hooking configuration or to a stored configuration. In another particular approach, the treatment device is embodied in an elongate member insertable through the skin capable of expanding at least one region from a smaller state to a wider state, and when in the wider state is configurable to both hook and cut, slice or disrupt target septa. In one or more alternative or additional aspects, cutting or disruption is accomplished with electrical or thermal means such as mono-polar or bi-polar structures or a hot wire configured to address bleeding and ease cutting.

Moreover, a cutting device can include an electrical element which differentiates between fibrous septa and structures undesirable to be cut such as vessels and nerves by means of electrical characteristics. Tissue desired to be cut such as fat and septa have different electrical characteristics, for example impedance, when compared to vessels and nerves. The device may either automatically cut the tissue captured by the element based on its electrical characteristics or the device may include an indicator which notifies the user of the type of tissue or simply the un-interpreted electrical characteristic data. In cases where tumescence is utilized, it may be advantageous to use non-conductive fluids such as dextrose rather than saline to facilitate differentiation of tissue structures. In another aspect, the cutting element can deliver RF energy to facilitate cutting of the tissue. Additionally, the RF energy will promote coagulation of any vessels which are bleeding.

The cellulite treatment system also involves in certain approaches, illumination such as a bright light configured at or emitted through a tip of treatment structure or placed along or at strategic locations along treatment structure for the purposes of tracking advancement of the tool to the treatment site and locating intra-dermal structures at the treatment site. In this way, direct observation of the treatment device by transillumination through the skin is provided and positioning and performance thereof subcutaneously is readily available to an operator.

These and other features of the disclosure will become apparent to those persons skilled in the art upon reading the details of the systems and methods as more fully described below.

BRIEF DESCRIPTION OF THE DRAWINGS

FIGS. 8A-E are top views, depicting embodiments of hook and v-structure for treating cellulite.

DETAILED DESCRIPTION OF THE DISCLOSURE

Before the present systems and methods are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the preferred methods and materials are now described.

It must be noted that as used herein and in the appended claims, the singular forms "a", "an", and "the" include plural referents unless the context clearly dictates otherwise. Thus, for example, reference to "the system" includes reference to one or more systems and equivalents thereof known to those skilled in the art, and so forth.

Figure 1:
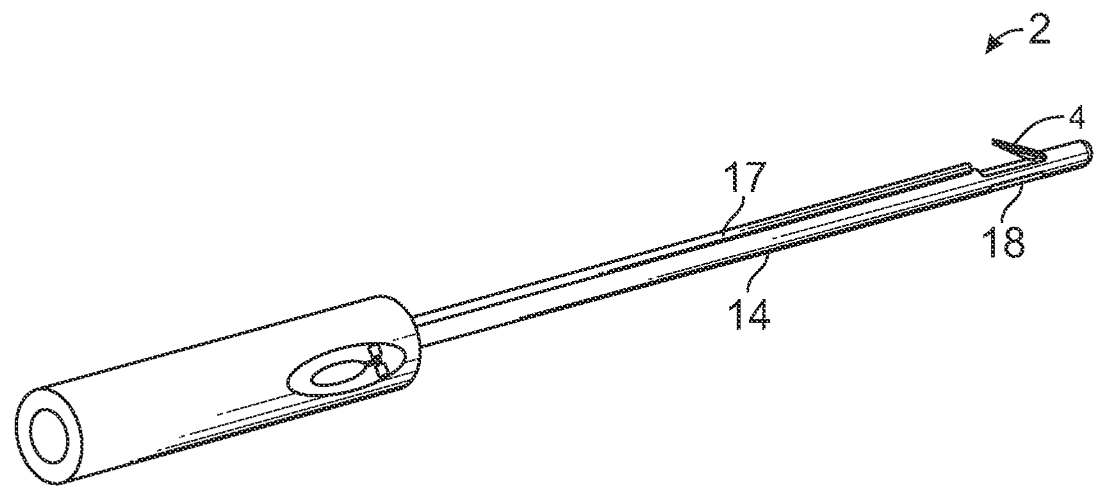
FIG. 1 is a perspective view, depicting a device for liposuction and cutting tissue.
Figure 2:
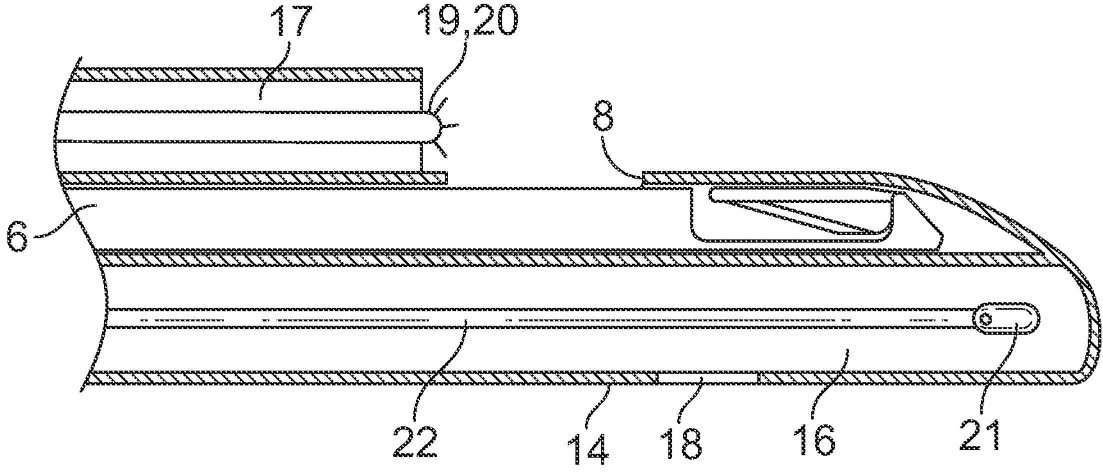
FIGS. 2-3 are cross-sectional views, depicting the device of FIG. 1 with a cutting element collapsed and expanded.
Figure 3:
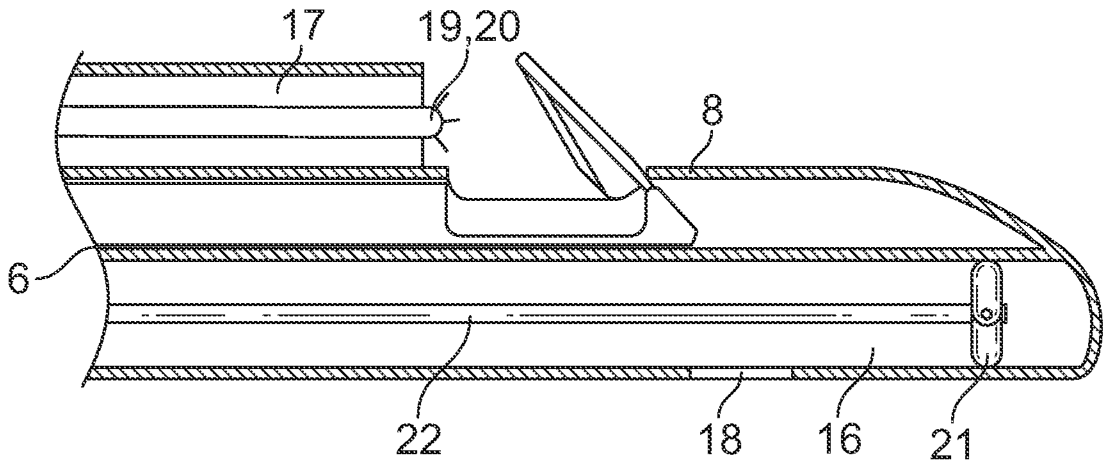

Referring to FIGS. 1-3, a liposuction and tissue cutting device 2 is shown. The device 2 is particularly suited for cutting septa while performing a liposuction procedure. Certain related features are disclosed in U.S. Pat. No. 8,652,123, the entire contents of which are incorporated herein by reference.

Treatment can be directed at various positions about connecting tissue or septa. That is, septa can be engaged, stretched, re-oriented, torn, cut, sliced, ruptured or disrupted from various sides or angles respecting septa and the treatment target location. Thus, septa can be treated from superior, inferior or medial or lateral locations from the septa and treatment target location to achieve the best results. For example, in a particular situation, treatment can be most effective from a position superior on the patient above a particular connecting tissue to take advantage of gravity where treatment forces placed on the connecting tissue coincide with the direction of gravity or the direction that gravity most often works on a standing body, as it has been observed that cellulite is often most visible in a standing individual.

Once selected or targeted septa are cut, sliced or disrupted, in each of the disclosed approaches, the treatment device can be or is advanced or repositioned to treat additional target areas from the same or different skin insertion location. In one embodiment, the treatment device embodies a hook and/or blade arrangement that is retracted or collapsed and stored for repositioning and then re-deployed for subsequent engagement and treatment of septa. Liposuction is performed as deemed necessary within or beyond the path cleared by cutting or disrupting septa.

Additionally, or alternatively, in each disclosed embodiment, illumination can be employed and provided via a lightguide from an external light source or via one or more LEDs external or internal the treatment device. Illumination aids the user both with locating the treatment device as well as proper depth placement as transillumination decreases with increasing tool depth. In one aspect, the amount of illumination is set to ensure proper depth of a treatment device or structure, the level of illumination targeted being adjusted for skin type, thickness, presence of fat and pigment.

In one approach, the treatment device 2 includes a mechanical cutting element 4 to cut tissue although as presented below, various other suitable cutting elements may be used. The cutting element 4 is movable from the collapsed position of FIG. 2 to the expanded or cutting position of FIG. 3. The cutting element 4 is coupled to a push rod 6 which is manipulated with a lever or slider on the handle to move the cutting element 4 between the stored and cutting positions. Notably, the cutting element 4 is configured near a terminal or distal end of the treatment device 2. The cutting element 4 is naturally biased toward the expanded position and is collapsed by advancing the push rod with a lever or slider (not shown) so that the cutting element 4 engages a shoulder 8 to force the cutting element 4 back to the collapsed position as the rod 6 is advanced. The cutting element 4 may have a first blade and a second blade to remove a section of the septa. Removal of a section, rather than simply cutting the septa at one location, may help to prevent the septa from reattaching during the healing process. In this specific regard, a clamping structure can be first used to clamp spaced points of targeted septa, and a cutting device (coring structure, RF, spaced blades or multiple cuts) can be used to remove a section of the septa between the clamped spaced points of engagement. In one aspect, the liposuction apparatus is employed to remove the cut section of the septa. Here as shown, first and second blades may be separated by at least 0.5 mm. As stated, it is understood that numerous aspects of the present invention may be practiced with different cutting elements such as RF, ultrasound or laser, or a single cutting element rather than two blades. Furthermore, cutting may be accomplished using blunt dissection.

The treatment device 2 includes an elongate body 14 having a lumen 16 extending therethrough. The lumen 16 leads to one or more openings 18 along the length of the body 14. In one aspect the opening 18 is positioned at or near a terminal or distal end of the treatment device 2. The lumen 16 is coupled to a source of suction so that suction may be used to draw fat and other tissue into the openings as is known in conventional liposuction. This lumen 16 is also configured to provide a path for clearing or creating space within the patient's anatomy. Fluid and/or gas can be passed through the lumen and inserted or deposited into the interventional area for insufflation to thereby create space for visualization or treatment. Moreover, the lumen 16 is configured to receive a dilation member (not shown) that can be used to create space. Additionally, a collapsible paddle 21 attached to an elongate member 22 extending to an operator can be configured within the lumen 16. After fat or other material is suctioned into the lumen 16, the paddle 21 can be deployed and the elongate member 22 can be withdrawn to clear the lumen 16 of collected material. The paddle 21 can then be collapsed and advanced again distally to be positioned for future use in clearing or removing tissue from the lumen 16.

The treatment device 2 may also have a lumen 17 which receives a visualization device 19 such as an endoscope, or is sized and shaped to receive a light source 20 for using transillumination. The endoscope can be on the order of about 4 mm in diameter or less or a light fiber providing the light source can be about 0.25 mm in diameter. Moreover, the light source 20 can be attached to or combined with the visualization device 19. The lumen 17 is positioned so that the user may view the tissue captured by the cutting element 4. The visualization device 19 may also be used to inspect the tissue prior, during and subsequent to cutting. In this manner, the user may deploy the cutting element 4 to cut septa and retract the element 4 when encountering large blood vessels or nerves. The visualization device 19 can further allow visualization of the distal tip of the cannula, which can prevent severe complications associated with undesirably puncturing body cavities.

One problem with conventional liposuction is that the liposuction wand will naturally be limited to a number of passageways or tunnels. It is often difficult to access the areas between these tunnels since the liposuction cannula will take the path of least resistance rather than penetrating new tissue. In particular, the septa 3 which interconnect the skin and muscle can be difficult to penetrate and can limit mobility of the cannula.

The cutting element 4 of the present invention permits the user to cut tissue adjacent to the liposuction structure. In this manner, the user can position the liposuction assembly in a tunnel adjacent to fat deposits that the user desires to remove but cannot reach due to the presence of tough septa. The cutting element 4 is positioned adjacent to the area where the user desires to remove additional fat deposits. The cutting element 4 is then expanded and moved proximally to hook and then cut tissue and, in particular, the septa adjacent to the body 14. The cutting element 4 is then retracted to prevent undesirable tissue damage. The body 14 is then moved so that a distal tip is positioned in the area where the tissue has been cut so that the user may access the tissue area adjacent the passageway using the same incision site. Although not shown, the cutting element 4 can also be distally-oriented, as opposed to proximally-oriented, in which case it is moved distally to cut tissue.

Treatment paths can be generated automatically by employing a computerized controller programmed to most efficiently address and measure a pre-defined treatment site. The computerized controller can be associated with a scanner that identifies specific areas for treatment such as by employing laser technology. In this regard, the computerized controller includes a program specific to liposuction and cellulite treatment and is used in conjunction with an electronic and mechanical device and comprises or includes a non-transitory computer-readable storage medium and a computer-program mechanism embedded therein to both identify treatment areas and to plot primary and alternative approaches to treatments. In another embodiment, computerized visualization and treatment planning equipment is used to assist the physician in determining insertion site locations and paths to be taken to the marked targets.

A measurement device can be employed to create a complete three-dimensional map of all target treatment areas. By dating and comparing treatment areas versus normal idealized surfaces, the operator calculates total and local volume benefits of therapy and track improvement over time.

Figure 4:
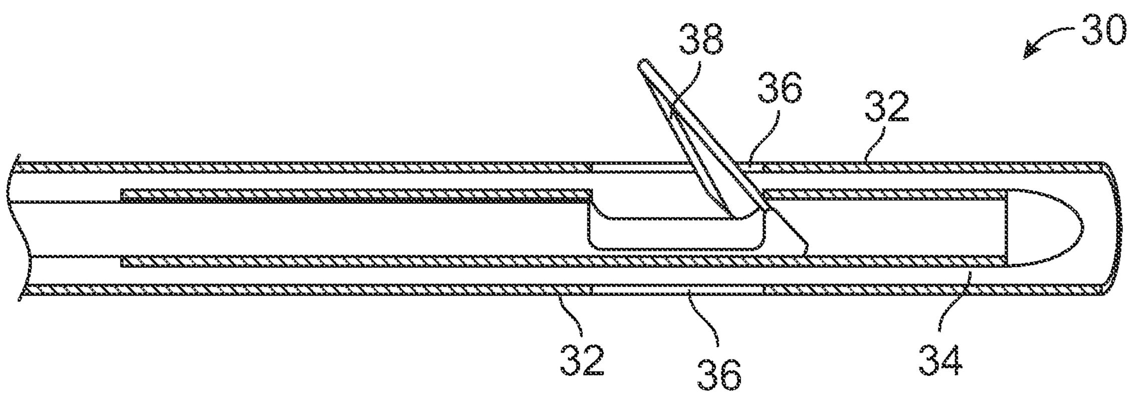
FIGS. 4-5 are top views in cross-section, depicting an alternative approach to a liposuction and cutting device.
Figure 5:
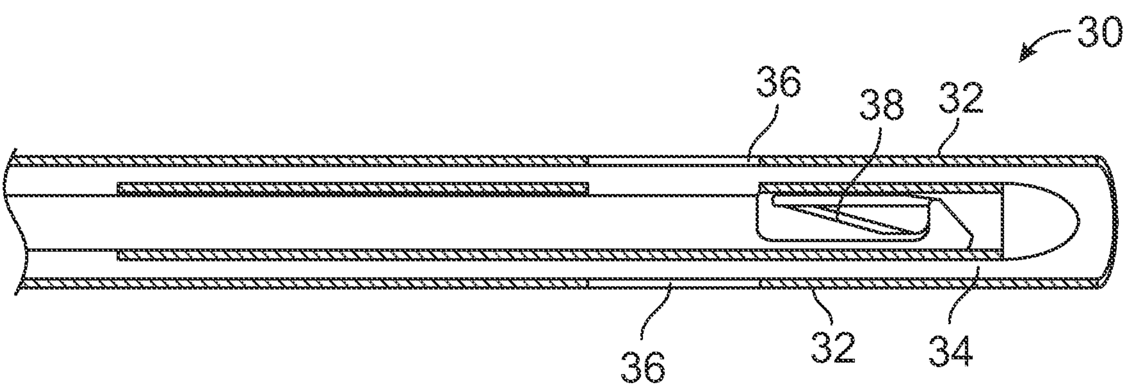

Referring to FIGS. 4-5, another treatment device 30 is shown for cutting tissue which may be used alone or in combination with a separate liposuction cannula. The device 30 includes a body 32 having a suction lumen 34 and one or more suction openings 36 which are used to remove fat and other tissue as described above. The device 30 also includes a cutting element 38 positioned inside the suction lumen 34. As shown, the distal terminal end of the device body 32 is open and as such the cutting element 38 can also be deployed through the distal terminal end as well as through openings 36. The cutting element 38 can also be sized to close the distal terminal end of the device body 32 and thus act as the terminal end tip structure. In an alternative approach, the distal terminal end of the device body 32 can include a cap or be closed independently of the cutting element 38. The cutting element 38 is movable from a position contained within suction lumen 34 to a position outside the suction lumen 34. The cutting element 38 may also be used to enhance withdrawal of the material through the suction lumen 34. The cutting element 38 is similar to the cutting element 4 and the description of the cutting element 4 is applicable to the cutting element 38. It is to be recognized however that any of the disclosed cutting elements can be incorporated into this assembly.

An advantage of the treatment device 30 of FIGS. 4-5 is that the cutting element 38 may be advanced and withdrawn within the suction lumen 34 as needed. This permits the user to undertake a conventional liposuction procedure and, at the appropriate time, the user may advance the cutting element 38 within the suction lumen 34 so that that tissue may be cut. The cutting element 38 may also be advanced into the suction lumen 34 to enhance withdrawal of the tissue. The cutting element 38 may also be completely removed from the cannula 32 as well. Additionally, material removing structure such as paddle 21 can be inserted and manipulated as deemed necessary to remove collected tissues.

Figure 6A:
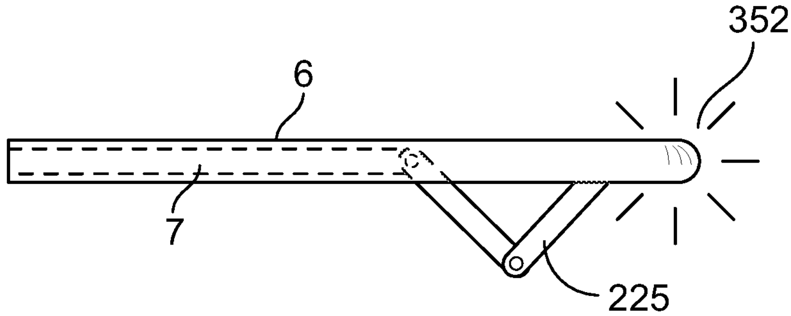
FIGS. 6A-B are top views, depicting another approach to a treatment device with an alternative cutting device.
Figure 6B:
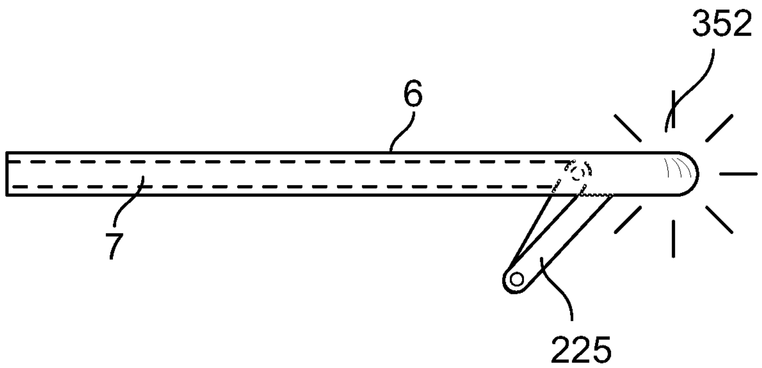

As shown in FIGS. 6A-B, there is a shown an alternative approach to a deployable cutting element 225 that can be used in combination with the treatment devices presented in FIGS. 1-5, in particular using first a hooking and then cutting element is advantageous when treating cellulite. The hooking and cutting device 225 is capable of one or more of engaging, stretching, slicing, cutting or disrupting connective tissue and is configured at a distal end portion of an elongate member or shaft 6. Controlled deployment and retraction of the hooking and cutting device 225 is provided by operator manipulation of a rod or other elongate member 7 within the shaft 6 attached to the hooking and cutting device 225. As such, the hooking and cutting element 225 can assume operator controlled completely open, closed, or partially open and/or closed configurations and the treatment device can lack element 8 (See FIGS. 1-3) for closing the cutting device. All cutting means can be combined with or further energized with RF, a laser, ultrasonic or thermal energy to produce cutting and coagulation together or separately. The disclosed interventional devices are configured such that a user can approach a target location and first use the interventional device to push, pull or otherwise tension septa in a target area under the skin to identify the specific septa impacting the target location and/or which is the cause of the expression of cellulite. In other words, pulling or pushing on the septa under the skin to find the one(s) that create the dimple or depression in the skin surface. For some treatment targets, taking an approach from an entry located inferior the treatment target, advancing the end of the interventional device with the hooking and cutting element collapsed beyond the treatment target and then extending the hooking and cutting element 225 and pulling inferiorly (effectively the “down” direction if the patient was standing) can provide an effective approach in locating the septa. For some treatment targets, taking an approach from an entry located superior the treatment target, advancing the end of the device with the hooking and cutting element collapsed beyond the treatment target and then pulling superiorly can provide an alternative effective approach. One or more strain gauges can be incorporated within the treatment device to help identify target septa as well as to assess the progress and completion of treating septa. In this context, the handle of the tissue treatment device can include a sensor and/or other electrical connection that when engaged or activated with a proximal end of the shaft 6, completes a circuit or otherwise permits energy to be provided to the cutting element 225. In this way, energy is provided to the cutting element when targeted septa is engaged, and energy is shut-off after septa engagement. This facilitates targeting of key septa in a less impactful way, ideally minimizing bruising or other issues associated with cutting or disrupting a large area around the target. A treatment regimen is selected for inserting interventional instruments based upon the subject's anatomy as it relates to the septa connecting tissue layers that define the chambers retaining fatty or other tissues. If desired, while anesthetic and/or sedation is taking effect, ultrasound can be used to assess the subcutaneous trajectory and depth of the various connective tissue bands responsible for the surface unevenness. The ultrasound evaluation can help with the particular trajectory selected for the desired depth. The ultrasound evaluation can also help with positioning the distal end portion of the treatment instrument strategically at the connection point between the connective tissue and the dermis or the facia.

In one aspect, a distal end portion of the treatment device is inserted through the skin and the blunt tip thereof is guided up into close proximity of the dermis as the tip can be tracked as it is advanced toward septa. A depth below the skin where septa is preferably engaged (i.e., cut, sliced, torn, stretched, re-oriented (e.g. crisscrossing) or disrupted) is identified and determined, by employing transillumination made possible by light source 352. After determining the subcutaneous depth to be accessed for the cutting, slicing, tearing, stretching, re-orienting (e.g. crisscrossing) or disrupting of septa, the treatment assembly or other tool with a sharpened or blunt tip is inserted through the skin, advanced between subcutaneous tissue layers and toward septa.

In one approach, a distal end portion of the cutting device 225 is configured with an illuminated tip 352 with enough brightness to be seen through the skin. The intensity of light emitted by the tip 352 can be set to a specific constant level such that at the preferred depth below the skin for severing or otherwise engaging septa, the light that appears at the level of the skin as a circle or projection is of a pre-determined size. Thus, the treatment device is advanced to the target site. At the target site, the user adjusts the depth of the tip of the treatment tool such that the circle or projection of light is the pre-determined size. The septa are tested and if confirmed as a target for treatment, the septa are treated while maintaining the circle or projection at the pre-determined size. The user can also use the size of the circle or projection of light to maintain the depth of the tip of the treatment tool as it is advanced under the skin to the treatment target. In an alternative or another aspect, a sharpened tip is employed to create access to target tissue thus allowing the tool to create the desired path both into tissue as well as between tissue layers. It is expected that in a septa cutting procedure where liposuction is not performed, the depth that these tools are advanced will be between about 3 and about 10 mm below the skin surface, but it is anticipated that lesser and greater depths may also be optimal for a particular subject. In any event, the depth selected is chosen for cutting, slicing, disrupting, tearing, stretching or re-orienting of the subject's septa. Moreover, in one embodiment, it is to be appreciated that the device 2 is formed from a substantially rigid material so that a consistent plane below the skin surface is accessed.

Using palpation, direct visualization (for example, transillumination or endoscopic) or non-invasive visualization (for example, ultrasound or fluoroscopic) or other means for determining the position of the interventional tool such as markings along the length of the instruments and its path within tissue, or providing the interventional instrumentation with radiopaque markers, the tool is placed at a site below where cellulite (for example a dimple) is seen on the subject's skin. The treatment device is advanced through septa and to where the treatment device 2 is in a position best suited to accomplish the identification of target septa and the cellulite removal or minimization treatment. In one approach, the treatment device 2 is passed beyond septa, a hook is deployed and then pulled proximally to tension septa, such as by hooking the septa. In another approach, the treatment device 2 is passed a few millimeters lateral, preferably about 1 to about 10 millimeters, more preferably about 3 to about 6 millimeters, and beyond the target location, a hook is deployed and then swept laterally toward the target followed by pulling proximally to hook and tension septa. During these and other steps, transillumination can be employed to track the treatment device and guide the procedure. Markings made on the skin surface while the patient is standing can facilitate targeting of septa while using transillumination to see the location of the treatment device 2 as it is advanced to the area under the markings on the skin surface by the physician. In other approaches, a separate device can be employed to engage septa to see if such septa are the source of a dimple or depression expressed on the outside of the skin. Such a secondary device can be placed remotely from the target (i.e. cellulite depression) and configured to be capable of applying tension to the surface of skin in a predetermined direction so as to create the effect of gravity and produce the visualization of the depressions while the patient is in a prone position (e.g., a broad region of adhesive attached to a spring mechanism such that a predetermined force would be applied relatively parallel to the surface of the skin in the direction the skin would move when standing in gravity). Using this additional device could further help the confirmation and location of depressions and allow confirmation that the treatment was effective. Also, in various approaches, a portion of the elongate member can be configured to transition from a smaller state to a wider or larger state, wherein in the wider or larger state a cutting surface (i.e. sharpened edge or energy) is presented to cut tissue, the device being sized and shaped to be inserted through the skin and engage one or more regions of septa subcutaneously.

It is noted that septa causing a dimple or depression may be coming from various angles and locations relative to the dimple or depression seen on the skin rather than being directly below the dimple or depression, and may be due to one or only a few septa or a large number of septa that remotely cause the depression or dimple. Thus, so engaging certain septa will be reflected in some change in the dimple or depression on the skin. A determination is made concerning the correspondence with marks made on the skin and the dimples being formed or re-formed. If the initial septa that the user presses on or pulls on using the tool do not recreate a dimple or depression in the marked area, then the user releases those initial septa that were engaged and repositions the tool at different septa and presses on or pulls again. This is repeated until the septa responsible for a dimple or depression in the marked location are identified. Once proper septa are identified, the treatment tool is manipulated to cut, slice, disrupt, re-orient, stretch or tear septum connecting tissue layers. In one approach, a blade is deployed and presented for treatment. In another approach, a balloon (not shown) is inflated to disrupt the septa.

After the proper septa have been cut, sliced, disrupted, stretched, re-oriented or torn, the treatment element is moved back to its initial collapsed configuration. Liposuction can be conducted or delayed until further septa are engaged and treated. The treatment element is then advanced beyond the marked treatment location, the treatment element (e.g., hook) is deployed and then pulled back under the marked treatment location to confirm that all of the septa responsible for causing the marked dimple or depression have been separated intra-operatively. If they have not been, the tool is manipulated to cut, slice, disrupt, stretch, re-orient or tear additional septa. The steps are repeated until all of the septa responsible for creating the marked dimple or depression have been severed or sufficiently stretched and the dimple or depression cannot be re-created intra-operatively using the tool. Such manipulation results in selective rupture, tearing, cutting or slicing of targeted septa, and the removal or minimization of dimples and the expression of cellulite on skin. Thereafter, the treatment element (e.g., hook and/or blade) is retracted back in and the tool 2 is removed from the site to be withdrawn from the body or repositioned in any direction along and within the target tissue plane to treat additional areas and to perform liposuction.

Figure 7A:
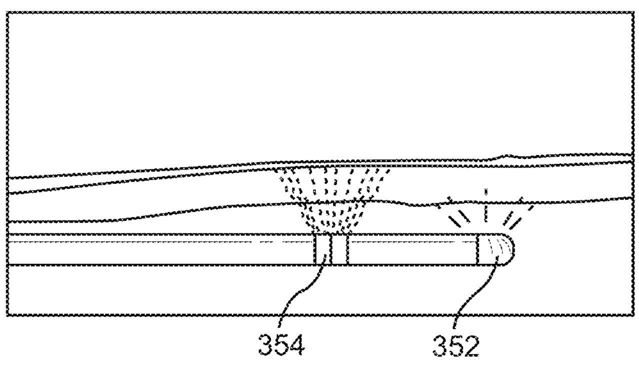
FIGS. 7A-D are side and top views, depicting a treatment device equipped with transillumination structure.
Figure 7B:
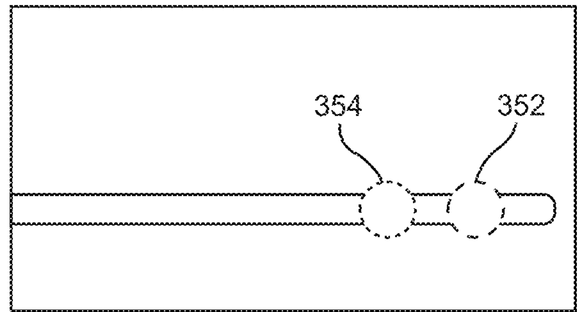
Figure 7C:
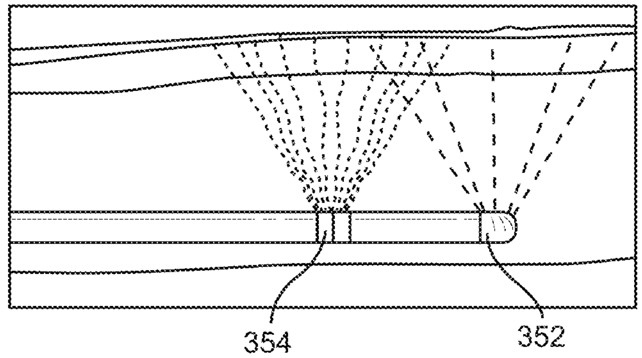
Figure 7D:
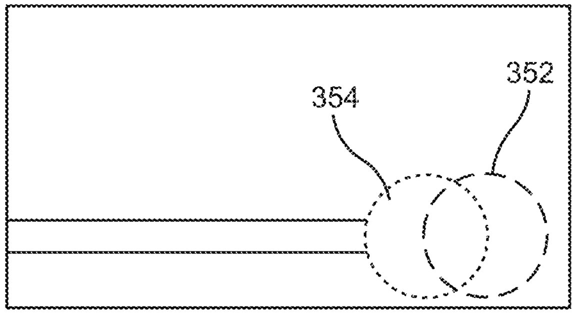
Figure 9A:
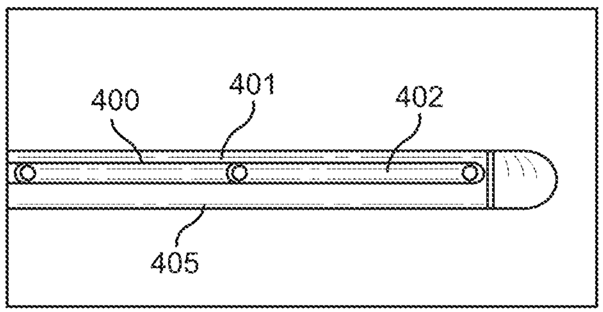
FIGS. 9A-D are top and partial cross-sectional views, depicting a treatment device with linkage hooking and cutting structure.
Figure 9B:
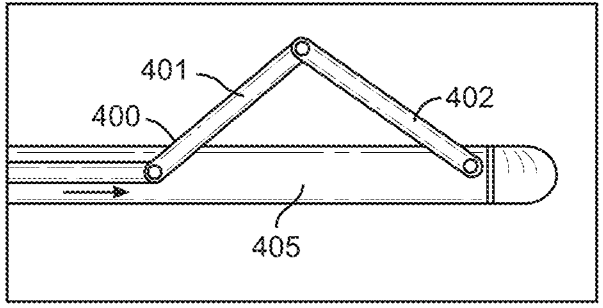
Figure 9C:
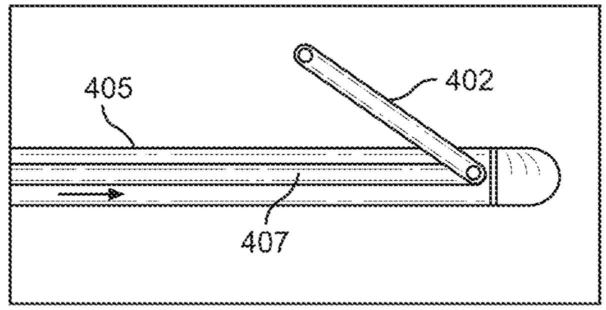
Figure 9D:
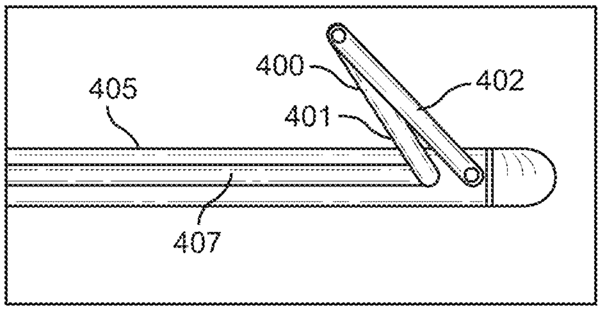

With reference to FIGS. 7A-D, in additional or alternative approaches, a second light source 354 such as an LED (or other light source) is configured along the treatment device assembly proximal the illuminated tip 352 or alternatively, at the tip 352. Such illumination sources (shown schematically in FIGS. 7A-D) can be placed along the septa cutting structure or along the treatment device itself, and can be incorporated into a liposuction cannula, such as at its tip, that is used independently of or without a cutting device. In various approaches, a light source such as an LED chip can be configured at the tip of or otherwise along the treatment device with an electrical wire running proximally for control by the operator, or the light source can be generated by a light fiber extending along the device or to the tip with the LED or light source is configured within a proximally located position such as a handle of the treatment device. By so configuring such light sources 352, 354, the depth of the treatment assembly within tissue can be assessed. As shown in FIGS. 7A-B, when the treatment assembly is placed within a first relatively shallow desired depth, the light sources 352, 354 appear spaced and define discrete patterns when viewing the light sources via transillumination through skin (FIG. 7B). When the treatment assembly is placed deeper within tissue (FIGS. 7C-D), the light sources 352, 354 overlap (FIG. 7D) due to the natural dispersion of light emitted from the light sources 352, 354. An operator of the treatment system can determine a depth of the treatment assembly by noting the discrete patterns of light or the degree of overlap of light overlap, the dispersion of light emitted and intensity of the light emitted from the light sources 352, 354. Thus, allowing the operator to guide the distal end of the treatment assembly to the desired treatment location while maintaining the desired depth below the skin. The light sources 352, 354 can also be of a different color to aid in determining the orientation of the treatment system within tissue through illumination. Moreover, the second light source 354 can emit a red color, for example, while the illuminated tip 352 can emit white light, while noting any variation of colors can also be employed. Also, the color of the light can change depending on the configuration of the treatment device, such as for example, the device can project a white or first color when sheathed or stowed and change to another color or second color when a portion of the device is deployed or before and after use such as when tissue is cut. A strain gauge can be configured to communicate and cooperate with the light source to sense loads placed on the treatment device during treatment to thereby facilitate a change in color of the light source and to signal the progress or completion of targeted treatment. Additionally, the second light source 354 can be employed via transillumination through skin to locate the treatment system relative to a treatment target area. Another benefit of the second light source is that it can indicate to the user where the hook and blade are located relative to the target septa. Also, as the treatment tool is being pulled proximally through the treatment target area, the illuminated tip 352 lets the user know when the hook and blade have been pulled through the target area. It is further noted that the light sources 352, 354 can be positioned at various alternative locations along a treatment device, and can be spaced from each other by various amounts. Also, the treatment system can include greater than two light sources of the same or dissimilar colors. In another embodiment, different colors of light can be used to indicate that the state of the distal end of the instrument. For example, red light is used to indicate the hook and blade are inside the instrument for advancing under the skin, white light is then used to indicate the hook is deployed, and red light is then used to indicate when the blade is deployed.

After completing treatment of one target area, the procedure is repeated to treat other target areas. Accordingly, the same device can be employed to access tissue layers below other liposuction sites or depressions existing in skin. Notably, in one embodiment, the device is capable of anesthetic delivery as needed or desired when progressing to additional or new locations. There is thus provided a system configured to treat all target areas on the buttocks and thigh through a limited number of small entry sites, including through a single entry site on a patient's treated side. It is to be recognized that the system can further include structure permitting the assembly to be steerable to subcutaneous treatment sites. In such an embodiment, the device would be configured to define longitudinally flexible material, and the instrumentation would be steered to the desired position within tissue. Moreover, in certain applications, the device has a stiffness that varies along its length. In another embodiment, the treatment device is embodied in a deflectable catheter.

Various alternative or additional approaches to laterally projectable tissue engaging and/or cutting structure or element for use in the disclosed treatment devices are shown in FIGS. 8A-E. The distal end portion of the cutting element can embody a side opening hook arm 370 that rotates with respect to a longitudinal shaft 372 to alternatively display septa engaging and/or septa cutting structure (FIGS. 8A-B). The hook arm 370 is configured to swing out from a proximally directed, longitudinal configuration where it is parallel with the shaft 372 to a laterally projected configuration to thereby capture and tension septa once the device is advanced beyond the target location and then retracted. Here again, so engaging septa can confirm that the septa responsible for creating skin surface dimples or depressions is being targeted as such engagement with septa will be reflected in a physical change of the skin surface. Disruption results from tensioning septa against a narrow edge of the hook arm 370 or against a cutting or sharpened edge thereof. An outward facing portion of the arm 370 can define blunt structure and a cutting edge can be positioned within the acute angle defined by the arm 370. With this structure, increased tension can be employed to cooperate with a limited cutting edge as septa is drawn within the acute angle defined by the arm 370. In FIGS. 8A-B, transillumination functionality is provided by a light 376 configured at a terminal end of the device, whereas in the assembly shown in FIGS. 8C-D, slits 378 formed in the shaft proximal the terminal end allow for the dispersion of light energy. In FIG. 8E, cutting and septa engaging structure is embodied in a single moving arm 380, while illumination is provided proximal to a hinge 382, but the same can be positioned at the terminal end of the device. As in the previous embodiments, the exposed edges of the arm 380 can be blunt or sharp for cutting or slicing. Also, here, the arm 380 assumes a distally directed, longitudinal configuration parallel to the shaft 372 for advancement between tissue layers, and the arm 380 is caused to be projected laterally outwardly to both capture and cut or slice target septa. Actuation of the engaging and cutting structures can be accomplished through the manipulation of a proximally positioned lever or trigger connected to the same via a wire or longitudinally directed shaft (not shown). Once a desired area is treated, additional target areas can be addressed. Again, liposuction can be performed intermittently or once an area is cleared of septa.

Referring now to FIGS. 9A-D, in alternative or additional approaches, the cutting, slicing or disrupting cutting element is defined by a projecting linkage arrangement. Such structure defines a cutting device for use with one or more of the disclosed treatment devices. A first link 400 includes a blade 401 and is rotatably attached at one end to a second link 402. The opposite end of the first link 400 slides with respect to a longitudinal shaft 405. A second end of the second link 402 is rotationally affixed to a distal point on the shaft 405. In one embodiment, as a drive shaft 407 attached to the opposite end of the first link 400 is advanced, the links 400, 402 fully overlap (FIG. 9C) to create a hook arrangement sized and shaped to engage tissues and to test septa to determine if such septa is associated with the expression of cellulite on a patient's skin. In this arrangement, the blade structure 401 is not exposed, but rather it is protected or covered by the second link 402. When cutting or slicing action is desired, such as once selected septa are targeted, the drive shaft 407 is slightly retracted, thereby exposing the blade structure 401 to thereby present a sharp edge for cutting of hooked septa (See FIG. 9D). To store the links 400, 402 away for advancement or repositioning between tissue layers, the shaft 407 is withdrawn completely which results in the links 400, 402 assuming a co-linear and parallel relationship with the shaft.

Figure 10A:
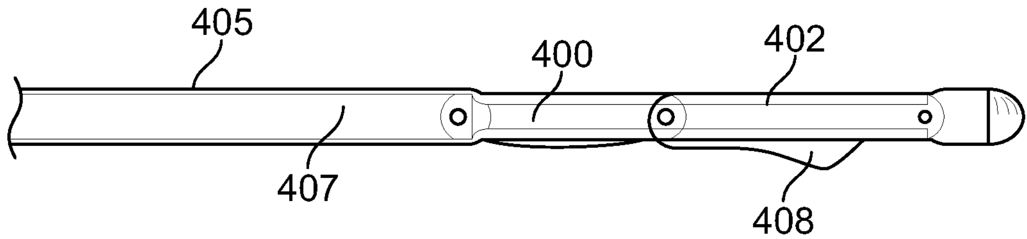
FIGS. 10A-G are top and partial cross-sectional views, depicting further approaches to a treatment device with linkage hooking and cutting structure.
Figure 10B:
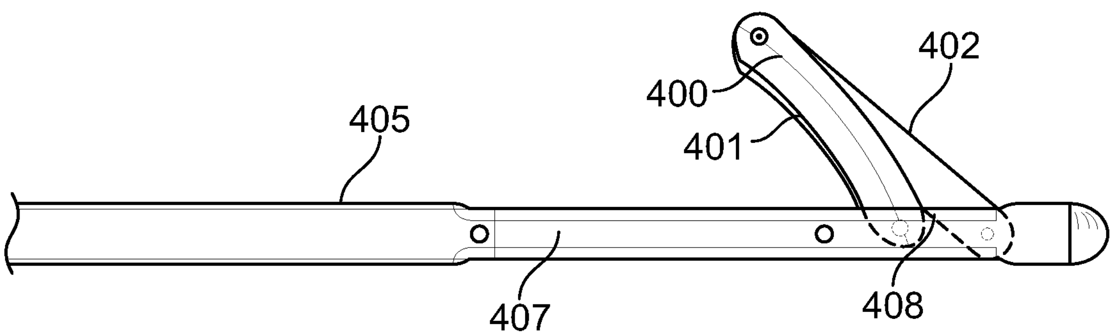
Figure 10C:
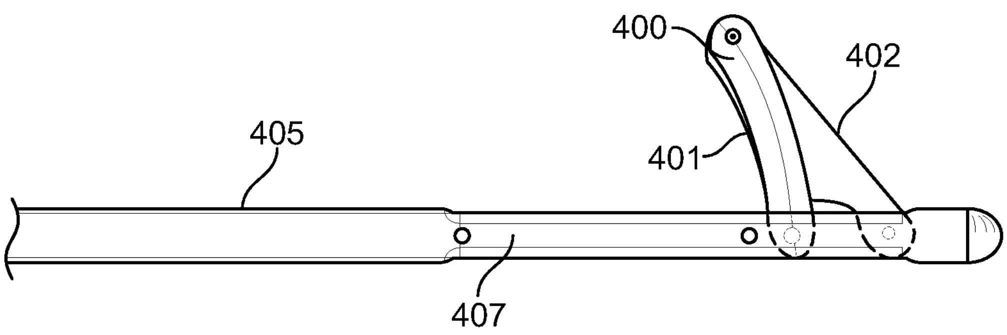
Figure 10D:
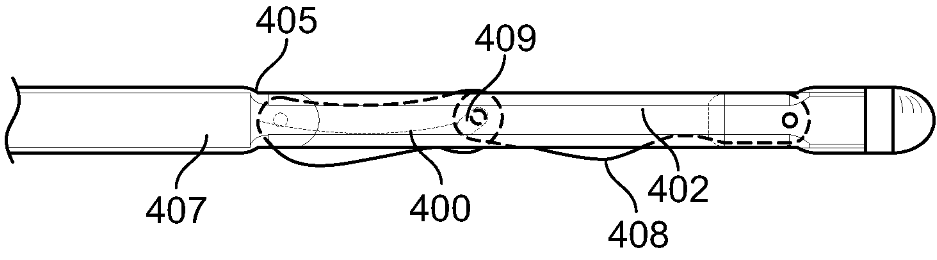
Figure 10E:
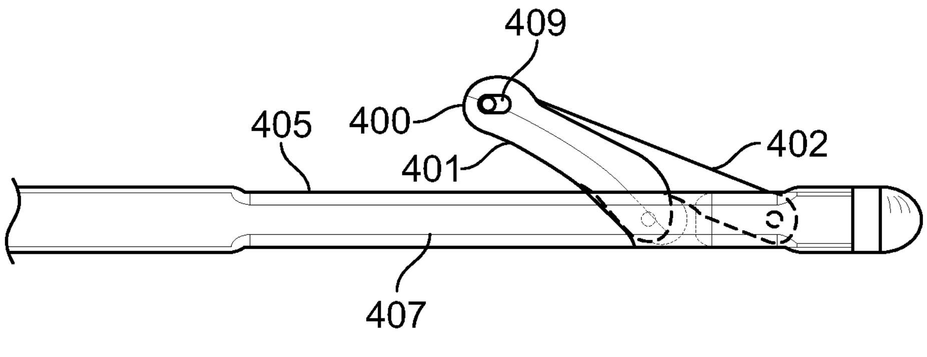
Figure 10F:
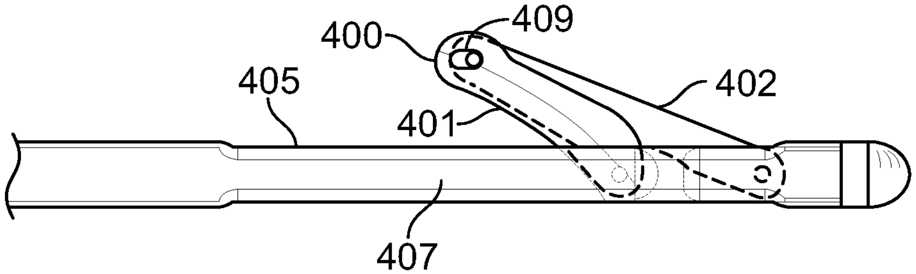
Figure 10G:
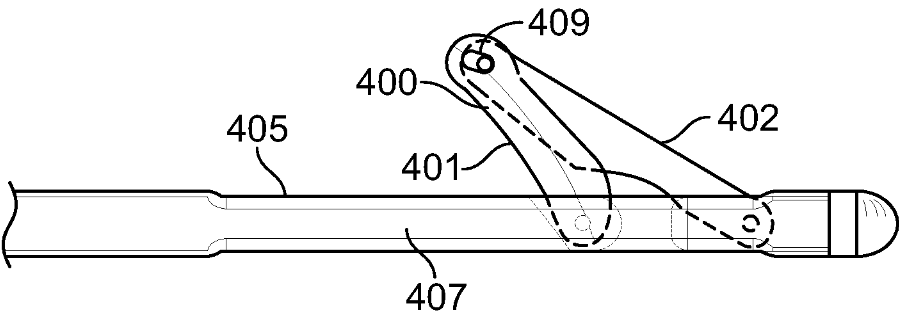

In a related approach to a cutting element for the treatment device, as shown in FIGS. 10A-C, the first link 400 defines a curved blade that is rotatably connected to a second link 402 that includes a generally triangular or pointed projection 408 that is sized and shaped to cover the blade 401 when the assembly is placed in a hooking configuration (See FIG. 10B). When the drive shaft 407 (shown in phantom lines) is manipulated such that the blade 401 is exposed (See FIG. 10C), the blade 401 can be employed to cut septa. When advancing the treatment device to and between interventional sites, the drive shaft 407 is withdrawn so that the assembly defines a lower profile where the first 400 and second links 402 are generally longitudinally aligned (FIG. 10A). As shown in FIGS. 10D-G, the rotatable connection between the first 400 and second links 402 can additionally or alternatively be characterized by a slotted arrangement 409. With such a connection, the projection 408 can be smaller, thus resulting in the overall profile of the treatment device being smaller. Notably, in a septa hooking configuration (FIG. 10E) after pulling the drive shaft 407 proximally slightly, an end of the first link 400 resides in a proximal position within the slot 409 and the smaller projection 408 of the second link 402 overlays the blade 401. Notably, positioning within the slot may change when the links are subjected to tension, such as when engaging septa. In a septa cutting configuration (FIG. 10G), the end of the first link 400 assumes a distal position within the slot 409 such that the blade 401 is exposed for cutting.

Figure 11A:
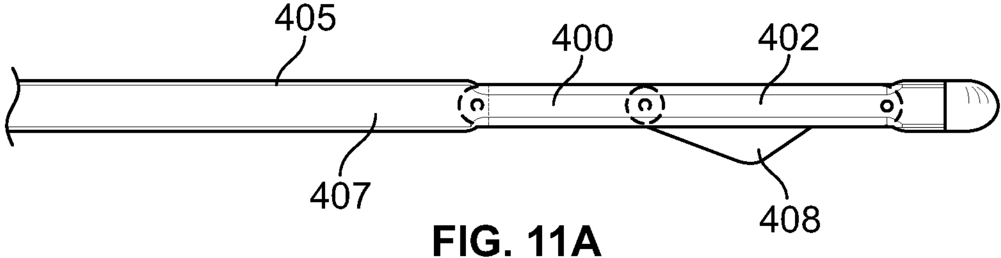
FIGS. 11A-C are top and partial cross-sectional views, depicting yet further approaches to a treatment device with linkage hooking and cutting structure.
Figure 11B:
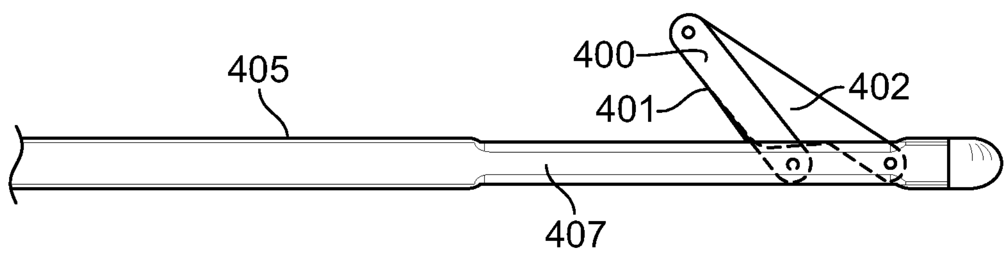
Figure 11C:
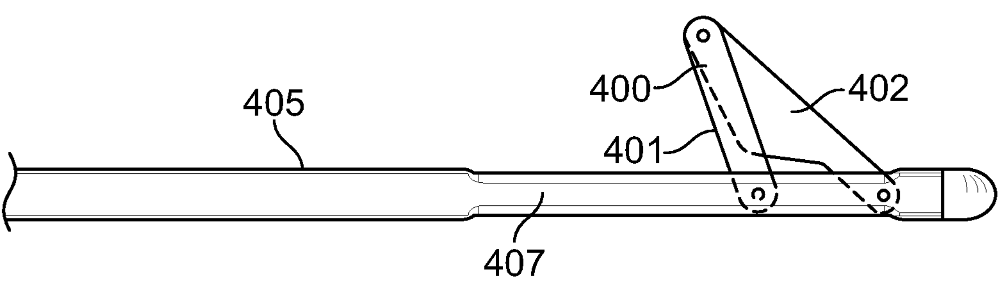

With reference to FIGS. 11A-C, in another approach to a cutting element to be used in combination with the treatment device, the first link 400 can also define a straight blade 401. In this approach, the projection 408 is larger to therefore provide necessary coverage of the blade 401 when the device is placed in a hooking configuration (FIG. 11B). Alternatively, the second link 402 can define a blade and the first link 401 is positionable to cover or block the second link 402. In yet a further embodiment, the second link 402 defines an RF electrode or other energy based cutting structure and the first link 401 is spring loaded such that when faced with a predefined load such as when engaging target septa, the drive shaft 407 would advance to trigger a switch. As first link 401 is moved out of the way, the energy based second link 402 is thus automatically activated to provide a cutting action based on tension. Notably, each of the foregoing devices can also additionally or alternatively include such structure or other of the features disclosed herein such as structure providing transillumination and radiofrequency cutting and coagulation. Moreover, alternatively, one or more of the disclosed distal links can be equipped with a blade and the disclosed proximal links can be configured as blocking structure.

Figure 12:
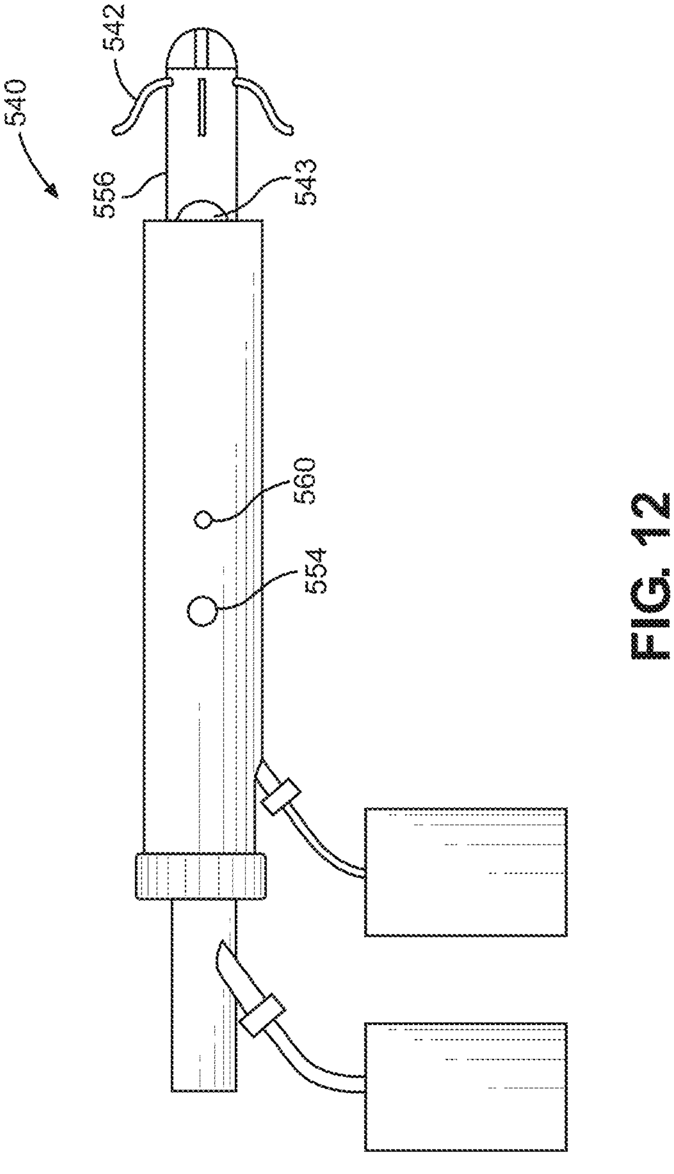
FIG. 12 is a top view, depicting another device for cutting tissue.
Figure 13:
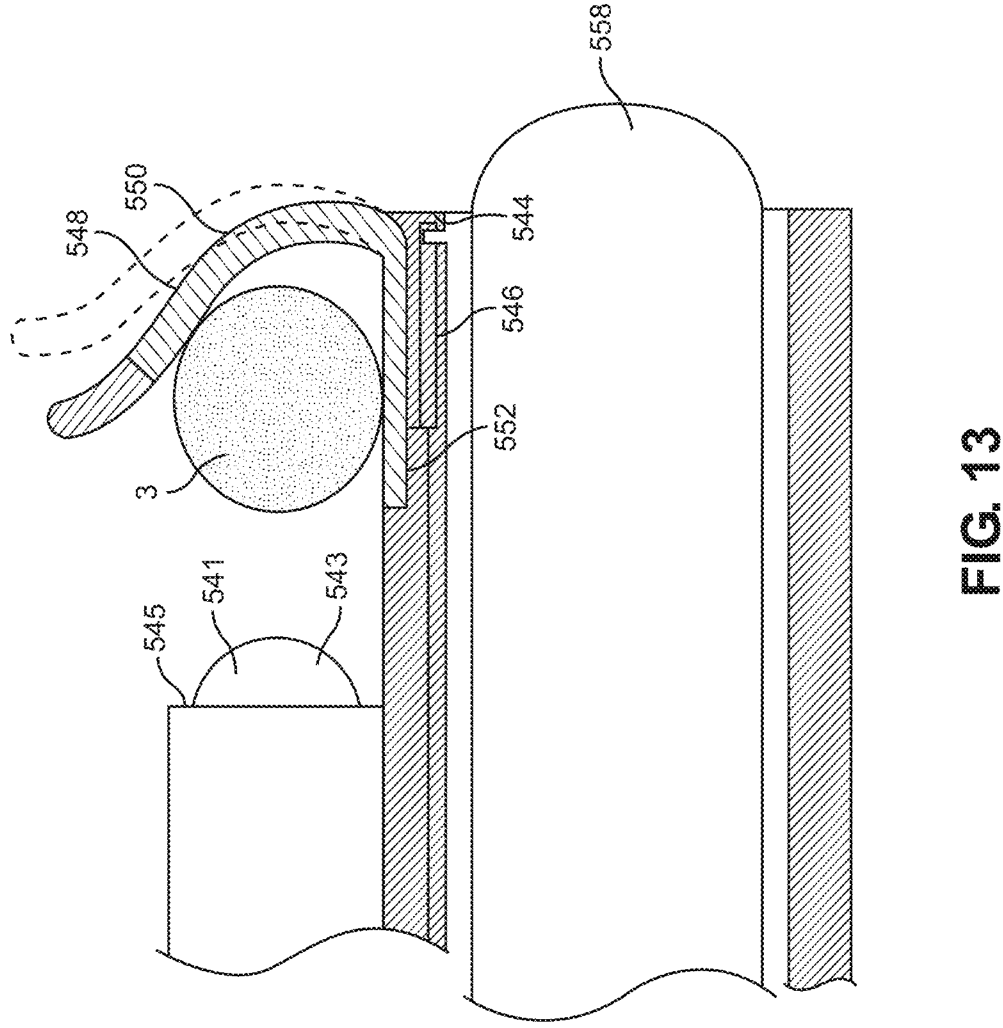
FIGS. 13-14 are cross-sectional views, depicting the device of FIG. 12 in use.
Figure 14:
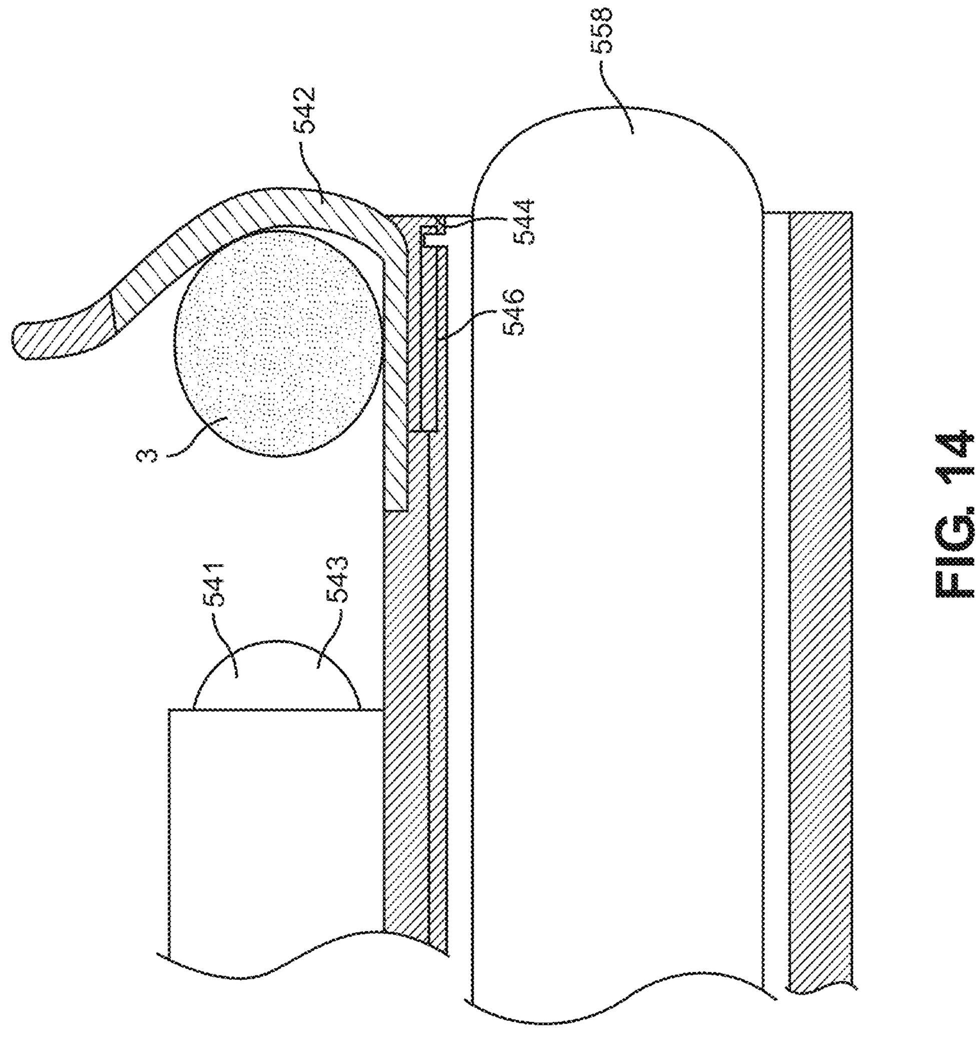

Referring now to FIGS. 12-14, another treatment device 540 is shown. The treatment device 540 has one or more elements 542 which can be deflected as the device 540 is moved through tissue. Such elements are positioned near a terminal or distal end of the treatment device 540 and can be configured to define deployable structure and/or structure that can alternatively be stiffened and made lax. Thus, each element can be defined by wires that can be withdrawn within the body of the treatment device. Alternatively or additionally, the elements 542 themselves can define structure that can be stiff or lax selectively by the operator or automatically by a computer control. Moreover, it is to be recognized that one or more of the previously disclosed approaches to cutting elements (FIGS. 8A-11C) can be incorporated into this device as elements 542, as well as the previously presented approaches to transillumination. In this way, the treatment device 540 can be passed through tissue to a treatment site without the elements 542 restricting movement. Once placed at an interventional or target site, the elements 542 are deployed or otherwise presented for engaging and assessing tissue. In one or more approaches, targeted tissue can be poked, clamped or otherwise captured by element 542 to measure stiffness and/or size of clamped/captured structures to identify the type of tissue engaged. Once target tissue is assessed, it can be cut or bypassed so that further tissues can be assessed or treated.

The embodiment of FIG. 12 has four elements 542 positioned at 90 degrees to one another around the body of the device 540. Again, the elements 542 can be deployable/retractable and/or define members that can be made of variable stiffness or made lax. Spacing the elements 542 in this manner reduces the need to orient the device 540 in order to capture septa. When fewer elements 542 are used, the element(s) 542 are oriented to capture tissue which extends between the skin and muscle when moved through tissue. The element 542 captures material with a hook-like structure. The element 542 can be deflected from the solid line position to the dotted line position of FIG. 13. Deflection of the element 542 may be used to distinguish relatively robust structures, such as septa, from softer tissues, such as blood vessels and nerves. Softer structures, such as blood vessels and nerves, may not be rigid enough to deflect the element and may be able to slip around the end of the relatively open hook-like element 542. The hook 542 may have smooth surfaces and transitions to minimize trauma to tissue and permit softer tissues to flow around the hook if the tissue is not robust enough to deflect the element. The element 542 may take any other suitable shape such as a V-shape.

Deflection of the element 542 may be recognized in any suitable manner. For example, a first contact point 544 on the element 542 may move into engagement with a second contact 546 as shown in FIG. 14. Of course, any other method of determining whether the element 542 has been deflected may be used. Furthermore, it is understood that deflection of the element 542 represents a threshold force required to move the element 542. As such, any other force-sensing element could be used including a piezoelectric element or a spring. The device 540 may also include a visualization device 541, such as an endoscope 543, to observe the tissue which has been trapped by the element 542. In this manner, the user may inspect the tissue which has been trapped prior to cutting. If the user does not want to cut the tissue which has been trapped, the user may simply manipulate the device 540 by collapsing the device 540 or gently rotating and/or advancing the device 540 to release the tissue which has been trapped. The endoscope 543 may be integrally formed with the device 540 or contained within a lumen 545.

If the element 542 is deflected as shown in FIG. 14, an indicator 560 on the device 540 may indicate to the user that the element 542 [442] has been deflected. At this time, the user may activate a cutting mechanism 548 to sever or cut the material captured by the element 542. The cutting mechanism 548 may be any suitable cutting mechanism with FIG. 13 showing an RF cutting element 548 but may also be an ultrasound element which delivers ultrasonic energy to cut the tissue. The RF cutting element 548 has a first electrode 540 and a second electrode 552 for bipolar RF but may be configured for monopolar RF as well. Notably, the electrodes 550 and 552 are positioned near the V-portion of the element 542 to present an effective cutting arrangement. The device 540 may operate to automatically activate the cutting mechanism 548 once the element 542 has been deflected or may require the user to activate the cutting element 548 using a push-button 554 or other suitable actuator. A cleaning mechanism can be incorporated into the area adjacent the cutting electrode in order to remove any char that may build up on the electrode after cuts are performed, for example small bristles inside of a sleeve can be advanced over and/or rotated over the electrode.

The element 542 may be coupled to a sleeve 556 which extends over a liposuction cannula 558 (FIG. 13). As such, the user may elect when, and if, the element 542 is used if at all. The sleeve 556 also permits the user to move the cutting element 548 longitudinally along the cannula 558 so that the cutting mechanism 548 may be used to selectively release septa without having to move the cannula as described above.

The element 542 may also be used for blunt dissection of tissue. The element 542 will capture and cut the septa by application of sufficient force to rupture the septa. The user may inspect the tissue using the visualization device 541 to distinguish septa from other tissue structures as discussed above before cutting tissue. A light source can be incorporated into the visualization device 541 or can define separate structure therefrom. Such a light source facilitates visualization at the interventional site, and can additionally be used for transillumination. Without the use of a visualization device, the user may also tug on the captured tissue to see if it is strongly connected to the skin or employ the sizing or electrical transmittance approaches to tissue identification. By evaluating the effect on the skin surface, tissues desired to be cut can be differentiated from those which are undesirable to cut.

Another way to distinguish structures desired or permissible to be cut such as septa and fat from tissues undesirable to affect, such as blood vessels and nerves, is to differentiate structures by their electrical characteristics. In an alternative approach, first and a second electrodes can be used in a bipolar configuration to measure electrical impedance of captured tissue. The electrode or electrodes can also be configured for monopolar measurements, which would require a reference electrode elsewhere on the subject. A skin electrode and a device electrode can be used. When the electrode on the device is primarily in contact with subcutaneous fat the impedance will be different than when the device electrode contacts the collagenis septa. When the system registers a change in the detected impedance, the system will alert the user. The same electrodes can be used to enact the cutting of the tissue. For example, the indicator may be used to determine whether the electrical impedance measured by the electrodes is within a threshold range which may help to distinguish blood vessels and nerves from septa. The device may operate to automatically activate cutting of the tissue or may require the user to activate the cutting element as described above in connection with the various disclosed embodiments.

Accordingly, various approaches to tissue treatment methods and apparatus are presented. The disclosed approaches are configured to provide an effective and focused approach to smoothing tissue and treating, minimizing and preventing cellulite. The disclosed approaches can also be used to repair and improve the appearance of tissue in a targeted manner. Further, the disclosed proactive treatment modalities are easy and effective to use. Additionally, the disclosed devices and structures are employed for body sculpting, eliminating wrinkles, treating acne scars and/or repositioning skin. Foam fillers or spacers of varying lengths and other structures such as subcutaneous attachment structures that are absorbable or permanent are used to accomplish such objectives.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the present disclosure.

That which is claimed is:

1. A method of disrupting a septum attached to skin using a device having a shaft, a disrupting element, and a sensing element, the method comprising:

moving the shaft below the skin to a treatment site;

contacting the septum with the sensing element;

pivoting the sensing element relative to the disrupting element to detect a force; and disrupting the septum with the disrupting element based on the force being greater than a threshold indicating contact with the septum.

2. The method of claim 1, wherein the sensing element is a link coupled to the shaft.

3. The method of claim 1, wherein the disrupting the septum is performed automatically when the sensing element detects the force greater than the threshold.

4. The method of claim 1, wherein the disrupting the septum is performed using radiofrequency energy.

5. The method of claim 1, further comprising:

indicating, with an indicator of the device, to a user that the sensing element detects the force greater than the threshold, wherein the disrupting is based on the user activating an actuator of the device.

6. The method of claim 1, wherein the disrupting element is selectively made stiff or lax.

7. The method of claim 1, wherein the disrupting the septum is operator controlled.

8. The method of claim 1, wherein the disrupting the septum is computer controlled.

9. The method of claim 1, further comprising deflecting the sensing element relative to the disrupting element to uncover the disrupting element when the septum contacts the sensing element.

10. The method of claim 1, further comprising retracting a drive shaft pivotably attached to the sensing element through the shaft when the septum contacts the sensing element.

11. A system for treating an expression of cellulite on skin of a patient, the system comprising:

a handle;

a shaft longitudinally extending from the handle, the shaft configured to be inserted through the skin and to be advanced under the skin to a treatment site;

a sensing element configured to contact a septum to detect a force applied by the septum;

a septa disrupting element at a distal portion of the shaft, wherein the sensing element is a link pivotably attached to the septa disrupting element; and an actuator configured to actuate the septa disrupting element based on the force being greater than a threshold.

12. The system of claim 11, wherein the septa disrupting element comprises a side opening hook.

13. The system of claim 11, wherein the septa disrupting element comprises a sharp edge.

14. The system of claim 11, wherein the shaft has a liposuction channel configured to be connected to a suction force, and a deployable paddle is in the shaft for removing material collected through the liposuction channel.

15. The system of claim 14, wherein the shaft has a plurality of openings in communication with the liposuction channel for collecting material removed from an interventional site during liposuction.

16. The system of claim 11, wherein the handle includes the actuator configured to controllably provide energy to the septa disrupting element to selectively cut the septum.

17. The system of claim 11, wherein the septa disrupting element comprises an expandable linkage and a blade.

18. The system of claim 11, further comprising a drive shaft extending through the shaft, wherein the sensing element is pivotably attached to the drive shaft.

19. The system of claim 18, wherein the drive shaft is spring-loaded.

20. The system of claim 11, wherein the sensing element covers the septa disrupting element in a first configuration, and the sensing element uncovers the septa disrupting element in a second configuration when the septa disrupting element is actuated.

21. The system of claim 11, wherein the septa disrupting element comprises an electrode.

22. The system of claim 21, wherein the electrode is configured to transmit radio-frequency energy when actuated.

23. The system of claim 21, wherein a deflection of the sensing element completes a circuit to transmit energy to the electrode when actuated.

24. A method of disrupting a septum attached to skin using a device having a shaft, a disrupting element, and a sensing element, the method comprising:

moving the shaft below the skin to a treatment site;

contacting the septum with the sensing element;

deflecting the sensing element relative to the disrupting element to detect a force and to uncover the disrupting element; and disrupting the septum with the disrupting element based on the force being greater than a threshold.

25. A system for treating an expression of cellulite on skin of a patient, the system comprising:

a handle;

a shaft longitudinally extending from the handle, the shaft configured to be inserted through the skin and to be advanced under the skin to a treatment site;

a sensing element configured to contact a septum to detect a force;

a septa disrupting element at a distal portion of the shaft; and an actuator configured to actuate the septa disrupting element based on the force being greater than a threshold, wherein the sensing element covers the septa disrupting element in a first configuration, and the sensing element uncovers the septa disrupting element in a second configuration when the septa disrupting element is actuated.

26. A system for treating an expression of cellulite on skin of a patient, the system comprising:

a handle;

a shaft longitudinally extending from the handle, the shaft configured to be inserted through the skin and to be advanced under the skin to a treatment site;

a sensing element configured to contact a septum to detect a force applied by the septum;

a drive shaft extending through the shaft, wherein the sensing element is pivotably attached to the drive shaft;

a septa disrupting element at a distal portion of the shaft; and an actuator configured to actuate the septa disrupting element based on the force being greater than a threshold.

27. The system of claim 26, wherein the drive shaft is spring-loaded.

* * * * *